United States Patent [19]

Marzolph et al.

[11] 4,456,772

[45] Jun. 26, 1984

[54] PROCESS FOR THE PREPARATION OF OPTIONALLY SUBSTITUTED FLUORO-NITRO-BENZALDEHYDES

[75] Inventors: Gerhard Marzolph, Cologne; Heinz U. Blank, Odenthal, both of Fed. Rep. of Germany

[73] Assignee: Bayer Aktiengesellschaft, Leverkusen, Fed. Rep. of Germany

[21] Appl. No.: 354,424

[22] Filed: Mar. 3, 1982

[30] Foreign Application Priority Data

Mar. 24, 1981 [DE] Fed. Rep. of Germany ....... 3111421

[51] Int. Cl.$^3$ ...................... C07C 79/36; C07C 45/63
[52] U.S. Cl. .................................................... 568/424
[58] Field of Search .............................. 568/424, 433

[56] References Cited

U.S. PATENT DOCUMENTS 3,064,058 11/1962 Duesel et al. ....................... 260/646

OTHER PUBLICATIONS

Pavlath et al., Aromatic Fluorine Compounds, (1962), 316–318.
Hudlicky, Chemistry of Organic Fluorine Compounds, (1962), 104–111.
Fieser et al., Reagents for Organic Synthesis, (1967), 934–935.
Fieser et al., Reagents for Organic Synthesis, vol. 2, (1969), 346.
Patent Abstracts from Japan, vol. 5, No. 71, (C-54), (743), May 13, 1981, JP A-56-20549.

Primary Examiner—Bernard Helfin
Attorney, Agent, or Firm—Sprung, Horn, Kramer & Woods

[57] ABSTRACT

Optionally substituted fluoro-nitro-benzaldehydes are prepared from optionally substituted halogeno-nitro-benzaldehydes and an alkali metal fluoride in a substantially anhydrous inert aprotic solvent, by heating to 50° to 250° C.

10 Claims, No Drawings

PROCESS FOR THE PREPARATION OF OPTIONALLY SUBSTITUTED FLUORO-NITRO-BENZALDEHYDES

The invention relates to a process for the preparation of optionally substituted fluoro-nitro-benzaldehydes by the reaction of optionally substituted halogeno-nitro-benzaldehydes with an alkali metal fluoride in an inert solvent.

Fluorine-containing benzene compounds, before the introduction of the aldehyde group or nitro group or both, have hitherto always been used as starting compounds for the preparation of fluoro-nitro-benzaldehydes.

Thus, in J.Chem.Soc. 1961, page 5418, the preparation of 5-fluoro-2-nitro-benzaldehyde from the expensive 3-fluoro-toluene is described, the methyl group first being converted into the aldehyde group by chlorination and hydrolysis, and the compound then being nitrated.

In Org. Synthesis, Col. vol. V, page 825, the preparation of optionally fluorine-substituted o-nitro-benzaldehydes is described, o-nitrotoluene being used as the starting compound and the appropriate substituted benzaldehyde being obtained throughout the stages of the benzylpyridinium bromide and the p-dimethylaminophenyl-α-phenylnitrone and its cleavage with sulphuric acid.

Furthermore, the nitration of 4-fluorobenzaldehyde to give 4-fluoro-3-nitrobenzaldehyde is known from Chem. Ber. 90, 1586 (1957).

The reaction of p-nitro-chlorobenzene with potassium fluoride in tetramethylene sulphone at 240° C. to give p-nitro-fluorobenzene is known from U.S. Pat. No. 3,064,058.

However, it is also known that potassium fluoride can be used in anhydrous media as a strongly basic catalyst, for example for decarboxylating cyclizations and condensation reactions with enclosure of oxo groups (Fieser, Reagents for Organic Synthesis, page 933, John Wiley and Sons Inc., 1967).

It has now been found, surprisingly, that the replacement of a halogen atom other than fluorine in halogeno-nitrobenzaldehyes can be carried out with an alkali metal fluoride, without side-reactions taking place at and with the aldehyde group under the influence of the alkali metal fluoride. In addition, the reaction can be carried out at surprisingly low temperatures.

The invention thus relates to a process for the preparation of optionally substituted fluoro-nitro-benzaldehydes of the formula

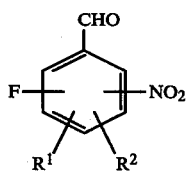

(I)

in which
R¹ and R² independently of one another represent hydrogen, alkyl, aryl or aralkyl, and furthermore, in the case in which fluorine and nitro are located ortho or para to one another, can denote a second fluorine atom located ortho or para to the nitro group, or a chlorine, bromine or iodine located meta to the nitro group, which is characterized in that a halogeno-nitro-benzaldehyde of the formula

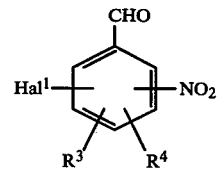

(II)

in which
R³ and R⁴ independently of one another represent hydrogen, alkyl, aryl, aralkyl, chlorine, bromine or iodine and
Hal¹ represents chlorine, bromine or iodine,
is reacted with an alkali metal fluoride in the presence of a polar aprotic solvent, at a temperature of from 50° to 250° C.

A straight-chain or branched aliphatic hydrocarbon radical having 1 to 20, preferably 1 to 10, particularly preferably 1 to 4 C atoms, such as methyl, ethyl, propyl, isopropyl, butyl, isobutyl, hexyl, isohexyl, octyl, isooctyl, stearyl or eicosyl, may be mentioned as an example of alkyl. Methyl or ethyl may be very particularly preferably mentioned.

Phenyl, diphenyl, naphthyl or anthryl, preferably phenyl, may be mentioned as examples of aryl. Substituents which contain phenyl, diphenyl, naphthyl or anthryl as the aromatic part, and the aliphatic part of which contains up to 4 C atoms, may be mentioned as examples of aralkyl. Benzyl is a preferred aralkyl.

The following may be mentioned as examples of halogeno-nitro-benzaldehydes which can be employed according to the invention: 4-chloro-3-nitrobenzaldehyde, 2-chloro-5-nitrobenzaldehyde, 5-chloro-2-nitrobenzaldehyde, 2,6-dichloro-3-nitrobenzaldehyde, 3-bromo-4-chloro-5-nitrobenzaldehyde, 2,4-dichloro-5-nitrobenzaldehyde, 2-chloro-4-methyl-5-nitrobenzaldehyde, 3,5-dichloro-2-nitrobenzaldehyde, 3,6-dichloro-2-nitrobenzaldehyde, 2,5-dichloro-3-nitrobenzaldehyde, 3,4,5-trichloro-2-nitro-benzaldehyde and 4-bromo-3,5-dichloro-2-nitrobenzaldehyde.

Such halogeno-nitro-benzaldehydes are known and can be prepared, for example by nitration, from the corresponding halogeno-benzaldehydes (Friedländer, Fortschritte der Teerfarbenfabrikation (Advances in Coal Tar Dye Production), volume 3, page 63, Verlag Julius Springer, Berlin 1896).

Halogeno-nitro-benzaldehydes of the formula

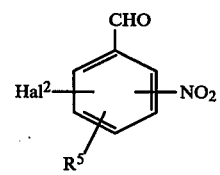

(III)

in which
R⁵ represents hydrogen, C₁–C₄-alkyl, phenyl, benzyl, chlorine or bromine and
Hal² represents chlorine or bromine,
are preferably employed.

Halogeno-nitro-benzaldehydes of the formula

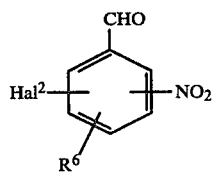

(IV)

in which
R[6] represents hydrogen, methyl or ethyl and
Hal[2] denotes chlorine or bromine, Hal[2] being located in the ortho or para position to the nitro group,
are very particularly preferably employed.

Sodium fluoride, potassium fluoride, rubidium fluoride or cesium fluoride, preferably potassium fluoride, may be mentioned as examples of the alkali metal fluoride for the process according to the invention. The alkali metal fluoride is employed in a quantity of from 1 to 10 mols, preferably from 1.1 to 3 mols, per equivalent of replaceable halogen atom. Sub-stoichiometric quantities of alkali metal fluoride lead to an incomplete reaction of the halogen-nitro-benzaldehyde. Although such a reaction is basically possible, it is not advantageous owing to the reduction in yield. It has been found that halogen which is located ortho or para to the nitro group can be more rapidly replaced by fluorine than a halogen in the meta position. In the case in which the halogeno-nitro-benzaldehyde to be employed as the starting material contains a second halogen atom, it is possible for this second halogen atom also to be replaced by fluorine if it, like the first halogen atom, is located at the ortho or para position to the nitro group. If, on the other hand, only the first halogen atom is located at the ortho or para position to the nitro group and the second halogen atom is located at the meta position to the nitro group, only the first halogen atom is, in general, replaced by fluorine.

The alkali metal fluoride to be employed should largely be dry. In this context, largely dry may be stated to be that which maintains a water content in the reaction mixture of at most 1% by weight, for example 0.001 to 1% by weight. The drying of the alkali metal fluoride can be carried out according to generally known methods. As a rule, drying at 170° to 200° C. in a drying cabinet, during a period of 5 to 10 hours, is quite sufficient.

The process according to the invention is carried out in a polar aprotic solvent. Such solvents are, for example, acid amides which are completely substituted at the nitrogen, such as dimethylformamide, dimethylacetamide, diethylformamide, diethylacetamide, N-methylpyrrolidone or hexamethylphosphoric acid triamide, and also sulphones, such as dimethylsulphone, tetramethylenesulphone or diphenylsulphone, furthermore sulphoxides, such as dimethyl sulphoxide, glycol ethers or polyglycol ethers, such as dimethoxyethane, diethoxyethane, diglymes or triglymes, or tetraglycol dimethyl ether, furthermore nitriles, such as acetonitrile or benzonitrile, and furthermore nitrobenzene. Among the acid amides completely substituted at the nitrogen, the N,N-disubstituted carboxamides are preferred; furthermore, the sulphones are preferred. The solvents mentioned can be employed individually or as mixtures of different stated substances. The quantity of solvent is proportioned such that it forms, together with the reactants, a readily stirrable suspension. 0.1 to 20 parts by weight of solvent or solvent mixture per part by weight of the sum of the halogen-nitro-benzaldehyde and the alkali metal fluoride, preferably 0.5 parts by weight to 5 parts by weight, may be mentioned as an example. The solvents mentioned, like the alkali metal fluoride, should be largely anhydrous for the process according to the invention, the abovementioned limits being applicable for the water content. This degree of dehydration of the solvent can be attained by methods which are in themselves known, such as the addition of an inert drying agent, incipient distillation of the solvent quantity until the required water content has been reached by azeotropic distillation of the water with a part of the solvent, or also by azeotropic distillation of the water from the solvent, using an entrainer for the water. Furthermore, it is possible to initially introduce the alkali metal fluoride and the solvent or solvent mixture, in which the salt or the solvent or both have a water content above the stated limit of 1% by weight, and then, by incipient distillation or by azeotropic distillation with the addition of an entrainer, to bring the water content of this salt/solvent suspension to the required level.

The process according to the invention is carried out at a temperature of from 50° to 250° C., preferably from 100° to 180° C. To control the reaction according to the invention, it can be advantageous to allow the solvent used to boil under reflux conditions. This reaction can also be carried out in a known manner at reduced or elevated pressure, in addition to atmospheric pressure. Establishing reflux conditions and, if appropriate, establishing a pressure which differs from normal pressure are not critical for the success of the process according to the invention.

The process according to the invention can be carried out both continuously and discontinuously.

The combination of the reactants and the solvent in the reactor can be carried out in any desired sequence. The solvent is often initially introduced into the reactor and the two reactants added to it. In this process, the halogeno-nitro-benzaldehydes are introduced into the reactor as a dry substance in solid or liquid form, if appropriate also as a solution in a part of the solvent used. If required, the water content of the solvent, if appropriate, also that of the alkali metal fluoride, can be adjusted, in the manner described above, to the required value, before the addition of the halogeno-nitro-benzaldehydes.

To isolate the optionally substituted fluoro-nitro-benzaldehydes, it is possible, for example, to distil off the solvent and to stir the remaining residue with water. The aqueous phase is separated off from the two-phase system formed thereby, and the organic phase is further worked up, for example by distillation, extraction or crystallization, to give the purified fluoro-nitro-benzaldehydes. The solvent which has been distilled off is largely recovered and can be re-used, if appropriate after purification.

However, in another variant of the working-up process, it is also possible to stir the total reaction mixture with water and to separate off the optionally substituted fluoro-nitro-benzaldehyde from this mixture, for example by filtration, extraction or also steam distillation.

The process according to the invention offers, in addition to the surprisingly uncomplicated practicability described at the beginning, a number of industrial advantages:

1. The fluorine atom is introduced only at the end of the reaction sequence. It is thereby possible to use cheap starting substances prodcued industrially on a large scale, for example chlorotoluene or chloro-benzaldehyde, which are converted in a known manner into the corresponding substituted chloro-nitro-benzaldehydes.

2. In comparison with other processes for introducing the fluorine atom by halogen/fluorine replacement, it is possible to carry out the reaction at advantageously low temperatures.

3. The difficult or expensive reagents, such as fluorine, hydrogen fluoride, boron trifluoride or tetrafluoroboric acid, which are used in many processes of the state of the art for introducing fluorine into an aromatic compound can be dispensed with in favor of the alkali metal fluorides which can be manipulated in an uncomplicated manner.

The fluoro-nitro-benzaldehydes which can be prepared according to the invention are valuable starting substance for the preparation of pharmaceutically active substances, for example for the preparation of fused pyrimidines which are employed in the treatment of allergies such as asthma (German Offenlegungsschrift No. 2,418,498; U.S. Pat. No. 4,044,134). Furthermore, they can be employed for the synthesis of benzylidenehydrazino-(1,2,4)-triazoles, which are suitable for the treatment of hypertension (South African Patent Application 7,703,470; quoted according to C.A. 89, P 146910 f).

EXAMPLE 1

4-Fluoro-3-nitrobenzaldehyde 93 g (0.5 mol) of 4-chloro-3-nitrobenzaldehyde and 58 g (1 mol) of potassium fluoride are suspended in 250 mol of dimethylformamide. The reaction mixture contains 0.02% of $H_2O$. The mixture is stirred for one hour at 160° C. and the dimethylformamide is evaporated off in vacuo. The residue is cooled and stirred with 200 ml of water, the mixture is extracted with methylene chloride and the organic phase is dried. After the methylene chloride has been evaporated off, 83 g of 4-fluoro-3-nitrobenzaldehyde with a content of 90.2% are obtained.

Yield: 88% of the theoretical yield.

After recrystallization, the 4-fluoro-3-nitro-benzaldehyde melts at 42° to 44° C.

EXAMPLE 2

2-Fluoro-5-notrobenzaldehyde 55.7 g (0.3 mol) of 2-chloro-5-nitrobenzaldehyde and 34.8 g (0.6 mol) of potassium fluoride are suspended in 250 ml of dimethylformamide and the mixture is stirred for 0.5 hours at 160° C. The mixture is then introduced into 600 ml of water and the aldehyde which has separated out is extracted with methylene chloride. The extract is separated off, dried and evaporated down. 48.9 g of 2-fluoro-5-nitrobenzaldehyde with a content of 94.8% are obtained.

Yield: 91% of the theoretical yield.

After recrystallization, the 2-fluoro-5-nitro-benzaldehyde melts at 53° to 54° C.

EXAMPLE 3

5-Fluoro-2-nitrobenzaldehyde 37 g (0.2 mol) of 5-chloro-2-nitrobenzaldehyde and 23.2 g (0.4 mol) of potassium fluoride in 300 ml of dimethylacetamide are stirred for 3 hours at 150° C. The solvent is then stripped off in vacuo and the residue is stirred with 200 ml of water. The aldehyde is extracted with methylene chloride, and the organic phase is separated off, dried and evaporated down. 24 g of 5-fluoro-2-nitrobenzaldehyde with a content of 86% are obtained.

Yield: 60.7% of the theoretical yield.

After recrystallization the 5-fluoro-2-nitro-benzaldehyde melts at 92° to 94° C.

EXAMPLE 4

18.6 g (0.1 mol) of 4-chloro-3-nitrobenzaldehyde and 6.4 g (0.11 mol) of potassium fluoride in 50 ml of dimethylformamide are stirred at 160° C. After 3 hours, 4-chloro-3-nitrobenzaldehyde is no longer detectable in the reaction mixture, according to gas chromatography. Instead, 4-fluoro-3-nitrobenzaldehyde has formed quantitatively.

EXAMPLE 5

18.6 g (0.1 mol) of 4-chloro-3-nitrobenzaldehyde and 8.7 g (0.15 mol) of potassium fluoride in 100 ml of sulpholane are stirred for 1 hour at 180° C. The mixture is stirred with 300 ml of water and the aldehyde is extracted with methylene chloride. After the customary working-up, 17.1 g of 92% strength 4-fluoro-3-nitrobenzaldehyde are obtained.

Yield: 92.5% of the theoretical yield.

EXAMPLE 6

18.6 g (0.1 mol) of 2-chloro-5-nitrobenzaldehyde and 11.6 g (0.2 mol) of dry potassium fluoride in 50 ml of dimethylformamide are stirred for 12 hours at 100° C. The solvent is then distilled off in vacuo and the residue is stirred in 100 ml of water. The crude 2-fluoro-5-nitrobenzaldehyde is filtered off under suction, washed with water and dried. 16.7 g of 2-fluoro-5-nitrobenzaldehyde with a content of 96% are obtained.

Yield: 94.8% of the theoretical yield.

What is claimed is:

1. A process for the preparation of 4-fluoro-3-nitrobenzaldehyde, 2-fluoro-5-nitrobenzaldehyde or 5-fluoro-2-nitrobenzaldehyde which comprises contacting 4-chloro-3-nitrobenzaldehyde, 2-chloro-5-nitrobenzaldehyde or 5-chloro-2-nitrobenzaldehyde with an alkali metal fluoride in the presence of a polar aprotic solvent which is an acid amide which is completely substituted at the nitrogen, a sulphoxide, a glycol ether, a polyglycol ether, a nitrile or nitrobenzene at a temperature from 50° to 250° C. whereby the chloro-nitrobenzaldehyde reactant is converted to the corresponding fluoro-nitrobenzaldehyde product.

2. A process according to claim 1, wherein the alkali metal fluoride is potassium fluoride.

3. A process according to claim 1, wherein the alkali metal fluoride is employed in an amount of 1 to 10 mols per halogen equivalent on said halogeno-nitro-benzaldehyde to be replaced by fluorine.

4. A process according to claim 1, wherein said alkali metal fluoride is employed in an amount of 1.1 to 3 mols per halogen equivalent to be replaced by fluorine.

5. A process according to claim 1, wherein said polar aprotic solvent is an N,N-disubstituted carboxamide or a sulphone, or a mixture thereof.

6. A process according to claim 1, wherein the water content of the reaction mixture employed is at most 1% by weight.

7. A process according to claim 1, wherein the process is carried out at a temperature of from 100° to 180° C.

8. A process according to claim 1, wherein the water content of the reaction mixture is between about 0.001% and about 1% by weight.

9. A process according to claim 1, wherein the amount of said solvent is between about 0.1 and about 20 parts by weight of solvent per part by weight of the sum of said halogeno-nitro-benzaldehyde and said alkali metal fluoride.

10. A process according to 1, wherein the amount of said solvent is between about 0.5 and 5 parts by weight of solvent per part by weight of the sum of said 4-chloro-3-nitrobenzaldehyde, 2-chloro-5-nitrobenzaldehyde, 5-chloro-2-nitrobenzaldehyde and said alkali metal fluoride.

* * * * *